United States Patent
Sticker et al.

(10) Patent No.: US 11,203,015 B2
(45) Date of Patent: Dec. 21, 2021

(54) MICROFLUIDIC DEVICE

(71) Applicant: TECHNISCHE UNIVERSITAT WIEN, Vienna (AT)

(72) Inventors: Drago Sticker, Malmo (SE); Peter Ertl, Vienna (AT); Sarah Lechner, Vienna (AT)

(73) Assignee: TECHNISCHE UNIVERSITAT WIEN, Vienna (AT)

( * ) Notice: Subject to any disclaimer, the term of this patent is extended or adjusted under 35 U.S.C. 154(b) by 82 days.

(21) Appl. No.: 16/093,072

(22) PCT Filed: Apr. 12, 2017

(86) PCT No.: PCT/EP2017/058855
§ 371 (c)(1),
(2) Date: Oct. 11, 2018

(87) PCT Pub. No.: WO2017/178552
PCT Pub. Date: Oct. 19, 2017

(65) Prior Publication Data
US 2019/0184394 A1    Jun. 20, 2019

(30) Foreign Application Priority Data
Apr. 14, 2016    (EP) .................................... 16165229

(51) Int. Cl.
*B01L 3/00*      (2006.01)
*C12M 3/00*      (2006.01)
(Continued)

(52) U.S. Cl.
CPC ....... *B01L 3/502715* (2013.01); *C12M 23/16* (2013.01); *C12M 23/20* (2013.01);
(Continued)

(58) Field of Classification Search
CPC ...................................................... C12M 35/04
See application file for complete search history.

(56) References Cited

U.S. PATENT DOCUMENTS

| | | | |
|---|---|---|---|
| 2005/0014129 A1* | 1/2005 | Cliffel | G01N 33/5038 435/4 |
| 2006/0134600 A1* | 6/2006 | Fuhr | C12M 33/02 435/4 |

(Continued)

OTHER PUBLICATIONS

Douglas C. Mcfarland: "Preparation of pure cell cultures by cloning", Methods in Cell Science Methods in Cell Science, vol. 22 Apr. 1, 2000 (Apr. 1, 2000), pp. 63-66, XP055312839.
(Continued)

*Primary Examiner* — Nathan A Bowers
(74) *Attorney, Agent, or Firm* — Workman Nydegger

(57) ABSTRACT

The present invention relates to a microfluidic device for creating within a cell assembly a cell-free area, comprising at least one cell chamber, wherein the at least one cell chamber comprises: —a fluid inlet for introducing fluid into the cell chamber, —a first area, —a second area, —at least one mechanical excluding means for excluding cells from the first area of the chamber and being operable between an excluding position and a releasing position optionally via an actuation line, wherein the second area of the cell chamber is outside of the operation range of the mechanical excluding means.

21 Claims, 7 Drawing Sheets

(51) Int. Cl.
    *C12M 3/06* (2006.01)
    *C12M 1/00* (2006.01)

(52) U.S. Cl.
    CPC ............ *C12M 23/34* (2013.01); *C12M 23/58* (2013.01); *B01L 2300/0861* (2013.01); *B01L 2300/12* (2013.01); *B01L 2300/16* (2013.01)

(56) References Cited

U.S. PATENT DOCUMENTS

| | | | |
|---|---|---|---|
| 2009/0088342 A1* | 4/2009 | Moraes | C12M 25/04 506/12 |
| 2009/0148880 A1* | 6/2009 | Fuhr | C12M 35/00 435/29 |
| 2010/0167382 A1* | 7/2010 | Fuhr | C12M 33/02 435/283.1 |
| 2011/0044865 A1 | 2/2011 | Groisman et al. | |
| 2014/0255961 A1 | 9/2014 | Prabhakarpandian et al. | |
| 2016/0067710 A1* | 3/2016 | Larsen | G01N 1/4077 435/25 |
| 2016/0194588 A1* | 7/2016 | Guenat | C12M 25/02 435/305.1 |
| 2019/0106671 A1* | 4/2019 | Richardson | G16B 50/00 |

OTHER PUBLICATIONS

International Search Report issued in PCT/EP2017/058855 dated May 24, 2017.

* cited by examiner

MICROFLUIDIC DEVICE

The present invention relates to microfluidic devices which can be used to create a cell-free area within a cell assembly and methods for using said devices.

Wound healing assays are commonly used in the assessment of cell motility and cell migration. In cancer research, such assays may provide a measure of the aggressiveness of metastasis and cancer cells and allow a rapid in vitro platform to test for drugs that inhibit metastasis and/or cancer growth. For burn patients, these assays provide a method to assess the speed of tissue regeneration and also a quantitative measure of the quality of wound repair, which may provide prognostic information about wound healing outcomes in these patients.

In general, cell migration involves the movement of cells in response to biological signals and environmental cues and plays a vital role in a variety of key physiological processes including immune cells recruitment, wound healing, and tissue repair as well as embryonic morphogenesis. For instance, in case of infections immune cells rapidly move from the lymph nodes via the circulation towards the infected site, while during wound healing cells steadily migrate to the injured tissue in a continuous attempt to repair the damage. In turn, abnormal cell migration resulting in the relocation of improper cell types to unsuitable tissue sites can lead to serious consequences such as mental retardation, cardiovascular disease, and arthritis as well as cancer metastasis and tumour formation. It has been recently recognized that only a better understanding of the complex, dynamic processes that govern cell migration will foster the development of novel therapeutic strategies to combat these diseases.

In vivo cell migration using state-of-the-art imaging methods poses serious limitations and ethical problems associated with animal testing. Therefore, in vitro migration assays are often used to investigate cellular mechanisms and multicellular movements.

Current in vitro methods to study cell migration are based on the inherent ability of adherent cells to move into cell-free areas. The introduction of cell-free areas within a cell culture layer can either be accomplished by cell exclusion using stamps to confine growth areas or cell depletion using electrical currents, (bio)chemicals and sharp objects to remove cells. All of these approaches have shown to exhibit similar migration pattern, since cells residing at the edge will migrate into the cell-free area independently of an prior cell-to-cell junction rupture. As a result, cell migration has also been used by biologists, pharmacologists, medical researchers and toxicologists to assess cell viability in cytotoxicity studies and broad-range screening applications to determine the health status of a cell population.

Compared to assays using cell exclusion, migration and wound healing assays based on the creation of cell depletion zones are predominantly performed to date for the analysis of cell movements in the absence and presence of external stimuli. A variety of approaches exist to induce wounds within a confluent cell monolayer, which can be separated into chemical (enzymatic), thermal (heating), optical (laser ablation) and mechanical removal of cells. An alternative method of creating defined depletion zones is based on the integration of electrodes to apply strong localized electrical fields to either lyse cells or prevent cell ingrowth (e.g. electric fence). Among these, the by far most popular cell depletion method is based on mechanical damage of cell surface layers, also called scratch assay. Hereby a cell-free area within a monolayer is created by manually scratching the cell culture surface using either plastic pipette tips or specialized blades to forcefully remove adherent cells from a surface. Quantification and analysis of cell motility is mainly accomplished by time-lapse microscopy and image analysis tools to determine time required to close the induced wound. Although scratch assays enjoy great popularity due to their simplicity and cost effectiveness, a number of problems are associated with manually inducing injuries such as reproducible wounding of defined areas, surface damage of the cell culture substrate and the release of intracellular compartments and chemical factors from injured cells, which are known to influence migration. Mechanical abrasion has shown to negatively impact cell-substrate interactions during cell migration, since the movement of a tip along a surface also effectively removes extracellular coatings and adhesion promoters, which are in many cases essential for cell attachment and spreading. In fact, assay reproducibility and reliably is greatly limited, because manual scratching essentially results in irregular cell-free areas and voids with jagged edges.

It is an object of the present invention to provide methods and means to overcome the drawbacks of the state of the art, in particular of the commonly used scratch assay.

The object of the invention is achieved with a microfluidic device for creating within a cell assembly a cell-free area, comprising at least one cell chamber, wherein the at least one cell chamber comprises:
- a fluid inlet for introducing fluid into the cell chamber,
- a first area,
- a second area,
- at least one mechanical excluding means for excluding cells from the first area of the chamber and being operable between an excluding position and a releasing position optionally via an actuation line, wherein the second area of the cell chamber is outside of the operation range of the mechanical excluding means.

It turned surprisingly out that with a microfluidic device according to the present invention it is possible to create—in a reliable and reproducible manner—a cell-free area within a cell assembly. In this state cells are only arranged in (i.e. limited to) the second area. Subsequently, cell migration into the cell-free area may be monitored. The mechanical excluding means is movable relative to the first area. The second area is outside of the operation range of the mechanical excluding means, i.e. cells may occupy the second area independently of the position of the mechanical excluding means.

In the excluding position the mechanical excluding means fills the space of the first area. In the releasing position the mechanical excluding means releases the space of the first area, such that cell migration into the first area may take place.

The cell-free area may be achieved with the mechanical excluding means by displacing cells from the first area and/or by preventing cells from being placed in the first area. The term "excluding" therefore comprises the options of (actively) removing cells from the first area and/or of (passively) acting as place holder preventing (from the beginning, i.e. already during cell seeding) that cells are placed in the first area.

Once a cell-free area is created the excluding means is moved to its releasing position and migration/proliferation of cells into the cell-free area may be monitored.

The actuation line that acts on the mechanical excluding means may be a pressure and/or vacuum transmitting line, such as a pneumatic line or a fluid line (using a medium such as gas or oil) but may also be an electric actuation line for driving the mechanical excluding means via an electric, magnetic and/or electromagnetic field. In fact, any type of actuation capable of moving the mechanical excluding means from the excluding position to the releasing position and/or vice versa would be possible for the purpose of the present invention. This means that also an externally applied magnetic and/or electromagnetic field capable to move the excluding means can be used. In such a case the excluding means preferably comprise ferromagnetic particles or are coated at least partially, preferably completely, with a ferromagnetic coating. The magnetic and/or electromagnetic field can be provided using one or more magnets and/or one or more electromagnets which are positioned nearby the mechanical excluding means. The use of electromagnets is particularly preferred because it allows to control the magnetic field by applying electricity so that the position of these electromagnets must not be changed after moving the mechanical excluding means.

In a preferred embodiment of the present invention the first area is substantially completely surrounded by the second area. This allows simulating an injury within living tissue. Usually, the injury is completely surrounded by healthy cells.

"Substantially completely", as used herein, means that at least 80%, preferably at least 85%, more preferably at least 90%, more preferably at least 95%, in particular 100%, of the first area is surrounded by the second area.

In a further preferred embodiment of the present invention the second area is at least as large as, preferably at least twice as large as the first area. This may allow the displacement of cells from the first area to the second area keeping the compression of cells in the second area relatively low.

In another preferred embodiment of the present invention the cell chamber is formed by a first wall and a second wall that is opposite to the first wall, wherein the mechanical excluding means forms in its releasing position at least a portion of the first wall and abuts in its excluding position against the second wall. In the excluding position the excluding means contacts the second wall thus completely filling the space of the first area. Preferably, the contact area of the mechanical excluding means with the second wall—in the excluding position—is between 0.2 mm$^2$ and 5 mm$^2$, preferably between 0.3 mm$^2$ and 4.5 mm$^2$, more preferably between 0.4 mm$^2$ and 4 mm$^2$, more preferably between 0.5 mm$^2$ and 3 mm$^2$.

In a preferred embodiment of the present invention the inner surface of the chamber wall that is opposite to the mechanical excluding means is substantially planar, preferably planar. Alternatively, the respective chamber wall may be convex or concave curved.

"Substantially planar", as used herein, means that the surface may have a flatness tolerance of less than 200 μm, preferably less than 100 μm, more preferably less than 50 μm.

In a further preferred embodiment of the present invention the inner surface of the chamber wall that is opposite to the mechanical excluding means is coated with at least one, preferably with at least two, more preferably with at least three, even more preferably with at least five, polypeptides and/or peptides, preferably with at least one cell adhesion promoter, which is preferably selected from the group consisting of fibronectin, fibrinogen, gelatin, collagen, laminin, poly-D-lysine and mixtures thereof.

Cells, in particular human and animal cells, show better cell adhesion and thus cell migration properties if they are incubated or grown on surfaces having adequate functionalities. Therefore, it is particularly preferred to coat the inner surface of the chamber wall that is opposite to the mechanical excluding means with appropriate polypeptides and/or peptides.

It is particularly preferred to coat the aforementioned inner surface with fibronectin, fibrinogen and/or gelatin. Preferred combinations of polypeptides include fibronectin, fibrinogen and gelatin, fibronectin and fibrinogen, fibronectin and gelatin and fibrinogen and gelatin.

In a preferred embodiment the operation range of the mechanical excluding means has essentially circular or polygonal shape and/or wherein the operation range of the mechanical excluding means has a diameter between 0.2 mm$^2$ and 5 mm$^2$, preferably between 0.3 mm$^2$ and 4.5 mm$^2$, more preferably between 0.4 mm$^2$ and 4 mm$^2$, more preferably between 0.5 mm$^2$ and 3 mm$^2$.

In a preferred embodiment the mechanical excluding means is formed by a flexible membrane. The use of a flexible membrane makes the process reliable, space-saving and easy to actuate using preferably a fluid like a gas (e.g. nitrogen, air, oxygen, carbon dioxide), water or oil. Depending on the fluid used the flexible membrane is preferably gas and/or water and/or oil impermeable.

Preferably, the membrane has a thickness between 10 μm and 500 μm, preferably between 20 μm and 500 μm, more preferably between 50 μm and 450 μm, more preferably between 100 μm and 400 μm, more preferably between 150 μm and 350 μm, more preferably between 200 μm and 300 μm. Preferably, the membrane comprises, consists of or is formed from polydimethylsiloxan (PDMS), thiolene-epoxy based polymers, fluorinated ethylene-propylene or a combination thereof and optionally a ferromagnetic coating and/or ferromagnetic particles.

If the mechanical excluding means of the microfluidic device of the present invention are moved by applying a magnetic or electromagnetic field, the membrane comprises preferably a ferromagnetic coating and/or ferromagnetic particles.

In a further preferred embodiment of the present invention the mechanical excluding means comprises a movable stamp, wherein the stamp is preferably integrally formed with a flexible membrane.

In another preferred embodiment of the present invention the mechanical excluding means is a displacement element for displacing cells from the first area and/or a place holder element for keeping the first area free from cells. As already mentioned above the cells may be actively removed from the first area and displaced to the second area (displacement element) or may be—from the beginning—passively kept away from the first area (place holder element).

According to a further preferred embodiment of the present invention the microfluidic device has, at least in the area of the at least one chamber, a sandwich structure with a top layer, an intermediate layer and a bottom layer, wherein the mechanical excluding means is formed by the intermediate layer. This allows a reliable, space-saving and cost-effective construction.

The second wall and the bottom layer are preferably optically transparent to allow transmission of light into and out of the cell chamber. The second wall and the bottom layer may be entirely transparent or at least transparent in the region of the first and/or second area. This transparency allows monitoring cell migration within the cell chamber of the device of the present invention.

"Optically transparent", as used herein, means that the material of the second wall and the bottom layer allows light of wavelengths ranging from 180 to 1500 nm, preferably from 220 to 800 nm, more preferably from 250 to 800 nm, more preferably from 280 to 600 nm, to be transmitted through the material with low or even no or substantially transmission losses. Such light transmissive materials include quartz, glass or polymeric materials which are preferably characterized by low crystallinity. Exemplary optically transparent and polymeric materials include polycarbonate, polyethylene terephthalate, copolymerized polyethylene terephthalate polyesters, polystyrene, polymethylpentene, fluorocarbon copolymers, polyacrylates (including polymethacrylates, such as polymethylmethacrylate (PMMA)), thiolene based materials, thiol-ene-epoxy based materials and others.

In a preferred embodiment of the present invention the side walls of the cell chamber are formed by the bottom layer and/or by the intermediate layer. The number of pieces that have to be assembled during production of the device of the present invention may be significantly reduced.

In another preferred embodiment of the present invention at least a portion of the actuation line is formed within the top layer. The integration of the actuation functionality into the top layer further reduces constructional efforts.

According to a preferred embodiment of the present invention the actuation line is a pneumatic line, a fluid line or an electrical conductor line.

The mechanical excluding means may be operated between an excluding position and a releasing position by various means. It is particularly preferred to provide one or more pneumatic lines to actuate the at least one mechanical excluding means. A pressure source connected to the pneumatic lines actuates the mechanical excluding means. The pressure source may use a gas like air, nitrogen, oxygen, carbon dioxide or any other gas. Alternatively the pressure source may also a liquid fluid like oil, an aqueous solution or water.

The excluding means can also be moved by magnetic or electromagnetic means. In such a case the excluding means are preferably coated by an electrically conductive material or a ferromagnetic material or would comprise ferromagnetic particles. The possible actuation line of a microfluidic device having this setup is either an electric conductor supplying the electromagnetic means or serves as a cavity to take up the excluding means.

In a preferred embodiment the at least one cell chamber comprises a fluid outlet, wherein a flow path is defined in the cell chamber between the fluid inlet and the fluid outlet. Cell migration may be monitored subsequent to and/or during supplying —at a certain flow rate—different media and/or substances such as drugs, nutrients, etc.

In a preferred embodiment in a cross section perpendicular to the flow path lateral areas of the cell chamber are outside of the operation range of the mechanical excluding means. This allows maintaining a flow rate also in the excluding position of the mechanical excluding means.

In a preferred embodiment the cell chamber and/or the microfluidic device has a flat cross section and/or elongated shape. The shape of the microfluidic device may be any one. However, it is particularly preferred that the cell chamber has an elongated shape.

The cell chamber is characterized by a height defined by an intermediate layer (e.g. mechanical excluding means) and a bottom layer. The cell chamber has also a width which is defined by side walls being located between an intermediate layer and a bottom layer. In some instances, the bottom layer may be formed of a single piece. The length of the cell chamber is defined by the fluid inlet and the fluid outlet. In a preferred embodiment the height of the cell chamber is smaller than 5 mm, preferably smaller than 4 mm, more preferably smaller than 3 mm, more preferably smaller than 2 mm, more preferably smaller than 1 mm, and may have a minimum height of 20 µm, preferably of 30 µm, more preferably of 40 µm, more preferably of 50 µm, more preferably of 100 µm, and/or wherein the width of the cell chamber amounts between 200 µm and 5 mm, preferably between 200 µm and 4 mm, more preferably between 200 µm and 3 mm, more preferably between 200 µm and 2 mm, and/or wherein the length of the cell chamber amounts between 2 mm and 10 cm.

In a preferred embodiment the microfluidic device comprises a plurality of cell chambers, preferably at least two, more preferably at least three, more preferably at least six, more preferably at least 12, more preferably at least 24, more preferably at least 48, more preferably at least 96, cell chambers.

Another aspect of the present invention relates to the use of a microfluidic device according to the present invention for monitoring cell migration or for performing a cell migration assay.

The microfluidic device of the present invention can be used to monitor cell migration or to perform cell migration assays.

In a preferred embodiment of the present invention the cell migration assay is used to test the influence of substances on cell migration.

The microfluidic device of the present invention can also be used in the assessment of the influence of certain substances in cell migration. This is a very useful tool to test how cell migration can be influenced by substances which can potentially be used in the treatment of diseases or conditions where cell migration plays an important role (e.g. wound healing, cancer). For this purpose the first area is made or provided cell free and the medium in which the cells are incubated within the cell chamber is conditioned with therapeutic substances or potential therapeutic substances.

In an alternative preferred embodiment of the present invention the microfluidic device can also be used to assess which pharmaceutically active substances out of a number of substances can be used in the treatment of patients in need of a therapy. This patient may suffer from cancer or may have a wound, for instance. In such a case cells of the patient are isolated and introduced into the microfluidic device of the present invention. These isolated cells adhere on the bottom layer of the cell chamber and grow thereon.

Another aspect of the present invention relates to a method for monitoring cell migration of human or animal cells, in particular of mammalian cells, comprising the steps of:

a. applying cells into at least one cell chamber of a microfluidic device according to the present invention to cover the second area and optionally the first area,
b. optionally bring the mechanical excluding means in an excluding position via an actuation line to displace or remove the cells from the first area,
c. bring the mechanical excluding means in a releasing position via an actuation line,
d. allow cell migration and monitor cell migration.

In a first step cells are applied to at least one cell chamber via the fluid inlet to cover at least the second area or at least a part thereof. The first area should be covered by the cells if the mechanical excluding means are not in contact with the bottom layer (i.e. first area) when applying the at least one cell chamber with the cells. In case the mechanical excluding means are in contact with the first area during applying the cells, this area will remain cell-free.

It is advantageous to incubate the at least one chamber for a certain period of time to allow the cells to adhere on the surface of the bottom layer accessible to the cells and cover substantially completely the second and optionally the first area. "Substantially completely", as used herein, means that at least 80%, preferably at least 85%, more preferably at least 90%, more preferably at least 95%, in particular 100%, of the second and optionally first area are covered by the cells.

In a second step cells present in the first area are displaced or removed. This is achieved by bringing the mechanical excluding means in an excluding position via an actuation line and results usually in killing the cells in the first area.

In order to allow the cells to migrate from the second area to the first area the mechanical excluding means has to be brought in a releasing position (i.e. the mechanical excluding shall not be in contact with the bottom layer of the cell chamber). It is advantageous to incubate the cells during step d) at a temperature which allows optimal cell growth.

According to a preferred embodiment of the present invention the at least one cell chamber is incubated before step a. with at least one polypeptide and/or peptide, preferably with at least one cell adhesion promoter, which is preferably selected from the group consisting of fibronectin, fibrinogen, gelatin, collagen, laminin, poly-D-lysine and mixtures for 10 min to 24 hours, preferably for 20 min to 12 hours, more preferably for 30 min to 6 hours, more preferably for 40 min to 3 hours, preferably at a temperature in between 20° C. to 38° C., preferably in between 25° C. and 38° C.

Human and animal cells, in particular mammalian cells, show a much better adherence to a non-biological surface if said surface is coated with a polypeptide or peptide. Thus, the surface of the bottom layer in the first and second area is coated at least partially, preferably entirely, as described above.

The microfluidic device of the present invention has—due to its structure—the advantage that the polypeptide or peptide coating is not removed from the surface of the bottom layer within the first and second area because no harsh chemical substances, no harsh physical conditions and no sharp object are needed to be used to remove the cells from the surface before starting with a migration assay. The simple application of pressure by the mechanical excluding means is enough to kill the cells which thereafter can be removed by one or more washing steps. The polypeptide and/or peptide coating remains thereby intact.

According to another preferred embodiment of the present invention the at least one cell chamber of step a. is incubated under conditions to allow the formation of a cell layer within the cell chamber covering the second area and optionally the first area.

The conditions under which the cells are incubated within the cell chamber depend mainly on the cell type used and are those known in the art to cultivate these cells. The conditions include temperature, medium, oxygen etc.

According to a further preferred embodiment of the present invention the at least one cell chamber of step a. is incubated for 10 min to 24 hours, preferably for 20 min to 12 hours, more preferably for 30 min to 6 hours, more preferably for 40 min to 3 hours, to allow adherence of the cells in the second area and optionally in the first area.

According to another preferred embodiment of the present invention the mechanical excluding means are abutted in its excluding position against the second wall by applying a differential pressure of 20 to 300 kPa, preferably of 50 to 250 kPa, more preferably 100 to 200 kPa, via the actuation line.

In order to kill and remove the cells within the first area or in order to prevent adherence of cells within the first area it is advantageous to apply a certain pressure.

In a preferred embodiment of the present invention at least one washing step is applied to the at least one cell chamber between each step.

A washing step is advantageous to remove death and non-adhering cells from the at least one cell chamber, for instance. The washing step has to be performed with solutions which do not negatively influence cell growth or affect the cells as such.

The cells can be cultivated using a continuous or non-continuous or interrupted flow of medium, preferably of fresh medium.

According to a preferred embodiment of the present invention cell migration is monitored by microscopy, preferably fluorescence microscopy or phase-contrast microscopy.

Cell migration can be monitored using several devices and methods whereby methods involving microscopy are most preferred.

According to a further preferred embodiment of the present invention the cells are stained before monitoring cell migration.

The cells are preferably stained with a wide range of dyes commonly used for labelling cells selected from the group consisting of Hoechst, Hoechst 33258, Hoechst 33342, Hoechst 34580, Calcein, Calcein AM, Calcein Blue, Calcein Blue AM, Calcium Green 1, Calcium Green 2, Calcium Green 5N, CoroNa Green, CoroNa Green AM, CoroNa Red, DiL, Fluo 3, Fluo 3 AM, Fluo 4, Fluo 4 AM, fluorescein dextran, Carboxyfluorescein succinimidyl ester (CFSE), and Texas Red dextran (see R. W. Sabnis, "Handbook of biological dyes and stains" Wiley 2010).

Alternatively, the cells are preferably genetically modified to express marker proteins, preferably fluorescent protein-based markers (e.g. green fluorescent protein, GFP). The use of cells expressing such proteins is particularly advantageous because no further staining is necessary since the genetic information encoding the proteins remains conserved in proliferated cells. Examples of suitable marker proteins are green fluorescence protein (GFP) and enhanced green fluorescent protein (EGFP).

Methods for introducing nucleic acid molecules encoding the above mentioned marker proteins are well known in the art.

The microfluidic device of the present invention allows to measure cell migration using any type of cells. Thus, the cells used in the method of the present invention can be tumor or healthy cells.

It is particularly preferred to use cells, preferably adherent cells, that are selected from the group consisting of endothelial cells, epithelial cells, fibroblasts, neurons, glial cells, stem cells, fat cells muscle cells and cancer cells.

Another aspect of the present invention relates to a kit comprising a microfluidic device according to the present invention and a microscope and/or a pump system.

The kit of the present invention may comprise a pump system which can be connected via the fluid inlet and optionally also the fluid outlet to the cell chamber and the microfluidic device, respectively. The pump system may comprise one or more valves and one or more pumps. Additionally the pumps and the valves of the pump system may be electronically controlled.

The invention will now be explained in detail by the drawings.

Figure 6:
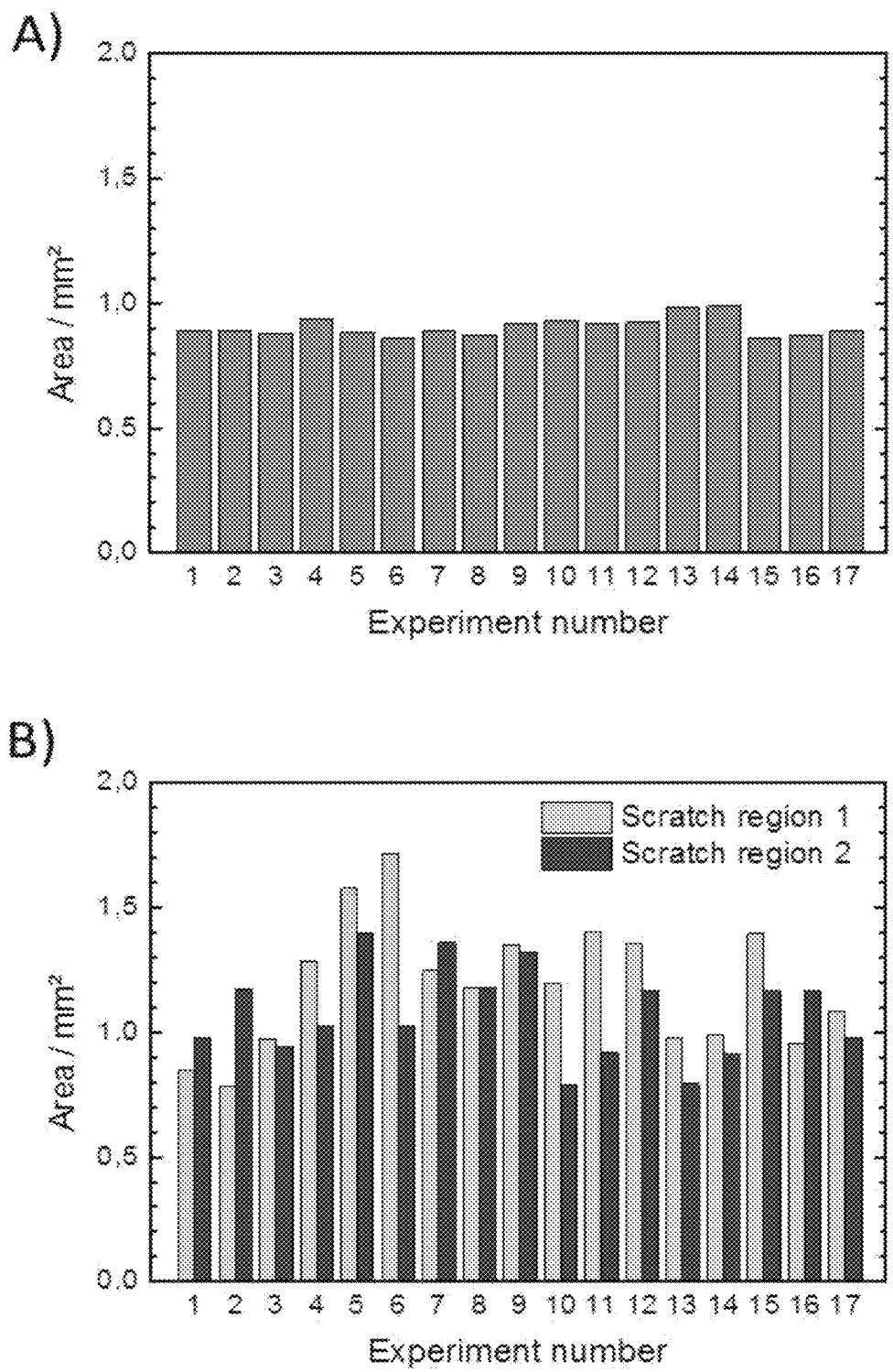
Figure 6:
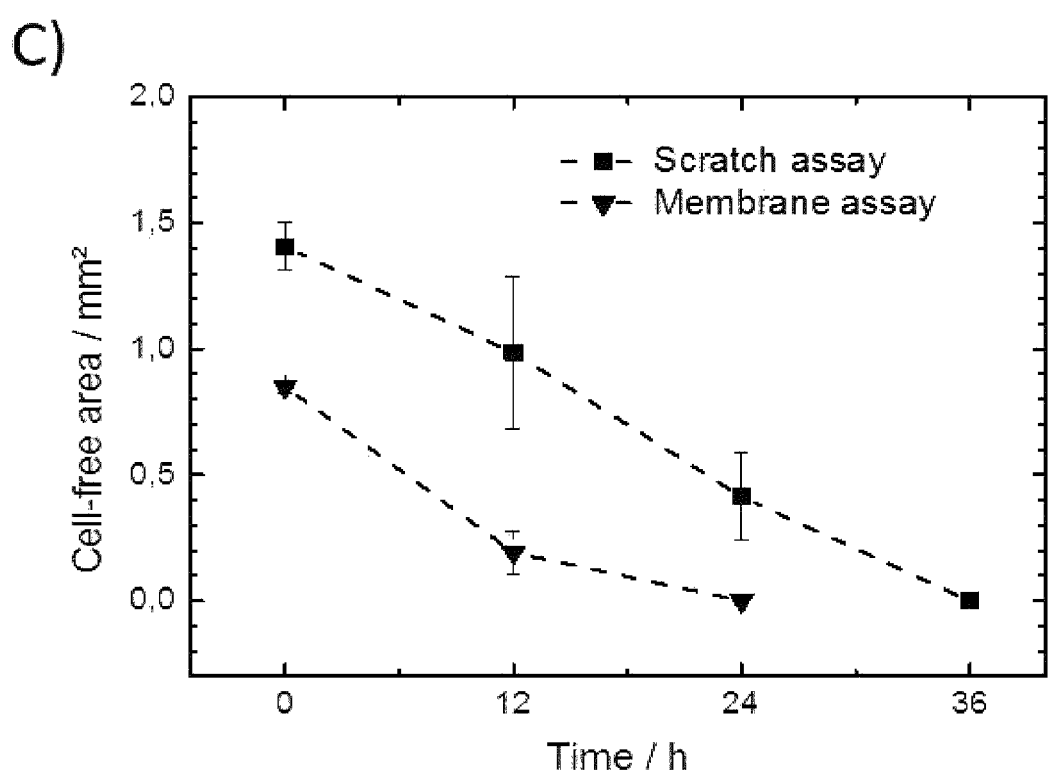

FIG. 6 shows A) measurements of wounded area in a epithelial cell layer from mechanical compression of the membrane. Histogram shows 17 independent experiments. B) Wound area resulting from 17 independent experiments with the classical scratch assay approach using a pipet tip. The area of two random regions along each scratch is presented. C) Measurements of HUVEC wound healing dynamics for scratch assay and microfluidic approach. The cell medium is supplemented with TNF-α. (n=3)

Figure 1:
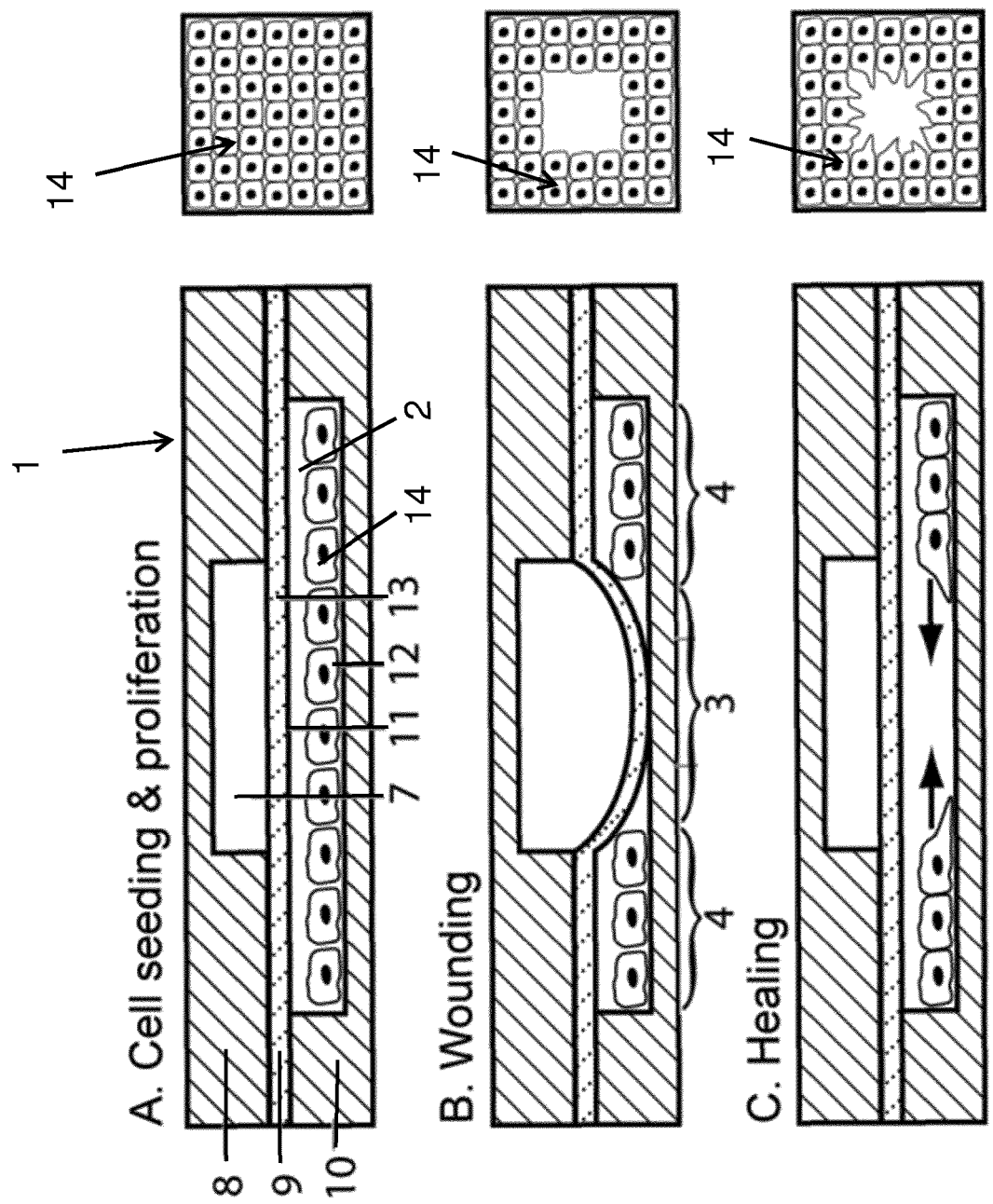
FIG. 1 shows in a cross-sectional view an embodiment of a microfluidic device in different operational stages.

The microfluidic device 1 of FIG. 1 comprises at least one cell chamber 2. The cell chamber 2 comprises a fluid inlet 5 for introducing fluid into the cell chamber 2 (FIG. 2), a first area 3, a second area 4, and a mechanical excluding means 13 for excluding cells from the first area 3 of the chamber 2.

The mechanical excluding means 13 is operable between an excluding position (middle part of FIG. 1) and a releasing position (upper and lower part of FIG. 1) via an actuation line 7.

In the embodiment of FIG. 1 the mechanical excluding means 13 is formed by a flexible membrane that is forced into the excluding position by pressure transmitted via the actuation line 7. The membrane may have e.g. a thickness between 10 µm and 500 µm, preferably between 200 µm and 300 µm and may be formed e.g. by Polydimethylsiloxan (PDMS) and/or Teflon.

The cell-free area—as can be seen from the lower part of FIG. 1—is achieved with the mechanical excluding means 13 by displacing cells from the first area 3 into the second area 4. At the beginning the first and second area 3, 4 are uniformly covered with a cell assembly 14. Then, cells located in the first area 3 are displaced by the excluding means 13. The second area 4 of the cell chamber 2 is outside of the operation range of the mechanical excluding means 13. Here, the first area 3 is completely surrounded by the second area 4. The second area 4 is at least as large as, preferably at least twice as large as the first area 3. When bringing the excluding means 13 into the releasing position again cell migration into the first area 3 is allowed (as indicated by the arrows).

The cell chamber 2 is formed by a first wall 11 and a second wall 12 that is opposite to the first wall 11. The mechanical excluding means 13 forms in its releasing position at least a portion of the first wall 11 and abuts in its excluding (or contacting) position against the second wall 12.

The inner surface of the chamber wall that is opposite to the mechanical excluding means 13 is substantially planar. Alternatively, a concave or convex curved shape would be possible.

The inner surface of the chamber wall that is opposite to the mechanical excluding means 13 may be coated with at least one polypeptide and/or peptide, preferably with at least one cell adhesion promoter, which is preferably selected from the group consisting of fibronectin, fibrinogen, gelatin, collagen, laminin, poly-D-lysine and mixtures thereof.

In the embodiment of FIG. 1 the operation range of the mechanical excluding means 13 has essentially circular shape. However, any other shape, e.g. polygonal shape would be possible. The operation range of the mechanical excluding means 13 may have a diameter (or contact area) between 0.2 mm$^2$ and 5 mm$^2$, preferably 0.5 mm$^2$ and 3 mm$^2$.

Figure 2:
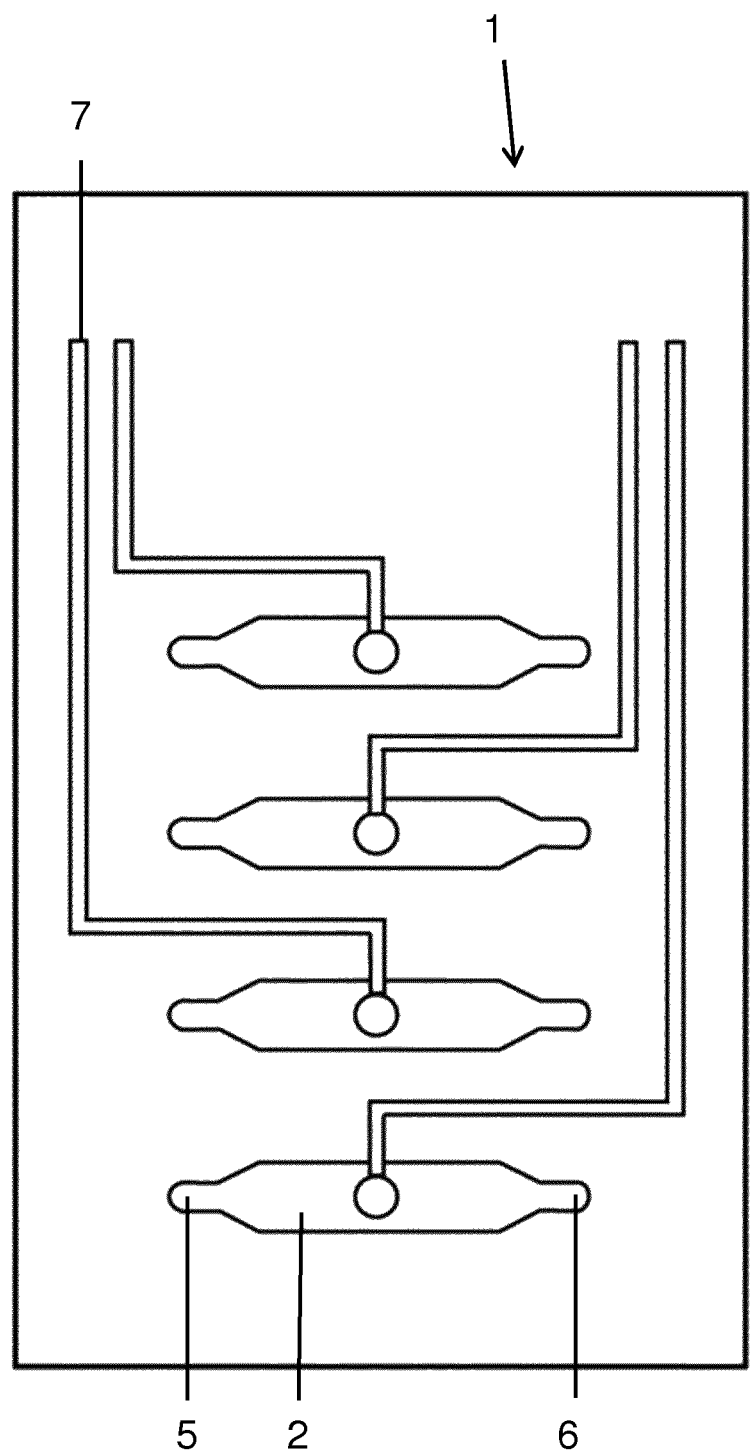
FIG. 2 shows in top view the microfluidic device of FIG. 1.

As can be seen from FIG. 2 the cell chamber 2 also comprises a fluid outlet 6, wherein a flow path is defined in the cell chamber 2 between the fluid inlet 5 and the fluid outlet 6. In a cross section perpendicular to the flow path (FIG. 1) lateral areas of the cell chamber 2 are outside of the operation range of the mechanical excluding means 13.

Figure 3:
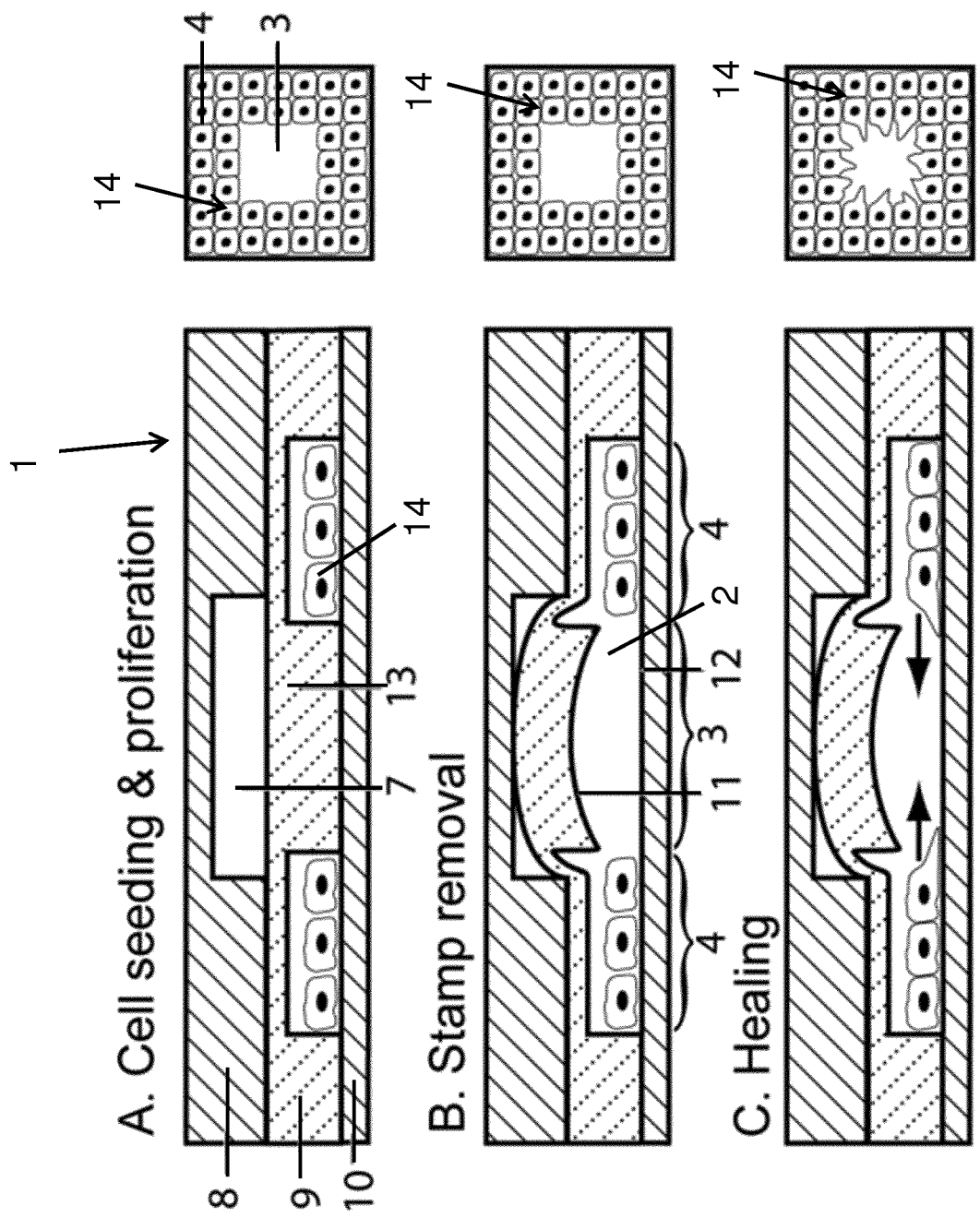
FIG. 3 shows in a cross-sectional view another embodiment of a microfluidic device in different operational stages.

While the mechanical excluding means 13 of FIG. 1 is used as displacement element for displacing cells from the first area 3, the excluding means 13 of FIG. 3 is used as place holder element for keeping the first area 3—from the beginning—free from cells. Here, the mechanical excluding means 13 comprises a movable stamp, which is integrally formed with a flexible membrane.

The excluding means 13 of FIG. 3 is in its excluding position already during cell seeding (upper part of FIG. 3). Subsequently to the cell seeding the excluding means 13 is operated to its releasing position (middle and lower part of FIG. 3) and cell migration into the first area 3 may take place. The movement of the excluding means 13 from its excluding position (upper part of FIG. 3) to its releasing position (middle part of FIG. 3) may be done by applying vacuum or under pressure to the actuation line 7 thereby sucking the membrane/stamp away from the first area 3.

In both embodiments (FIGS. 1 and 3) the microfluidic device 1 has a sandwich structure with a top layer 8, an intermediate layer 9 and a bottom layer 10, wherein the mechanical excluding means 13 is formed by the intermediate layer 9. The side walls of the cell chamber 2 are formed in FIG. 1 by the bottom layer 10 and in FIG. 3 by the intermediate layer 9. At least a portion of the actuation line 7 is formed within the top layer 8. As already mentioned the actuation line 7 may be a pneumatic line or a fluid line or an electric, magnetic or electromagnetic line.

Figure 4:
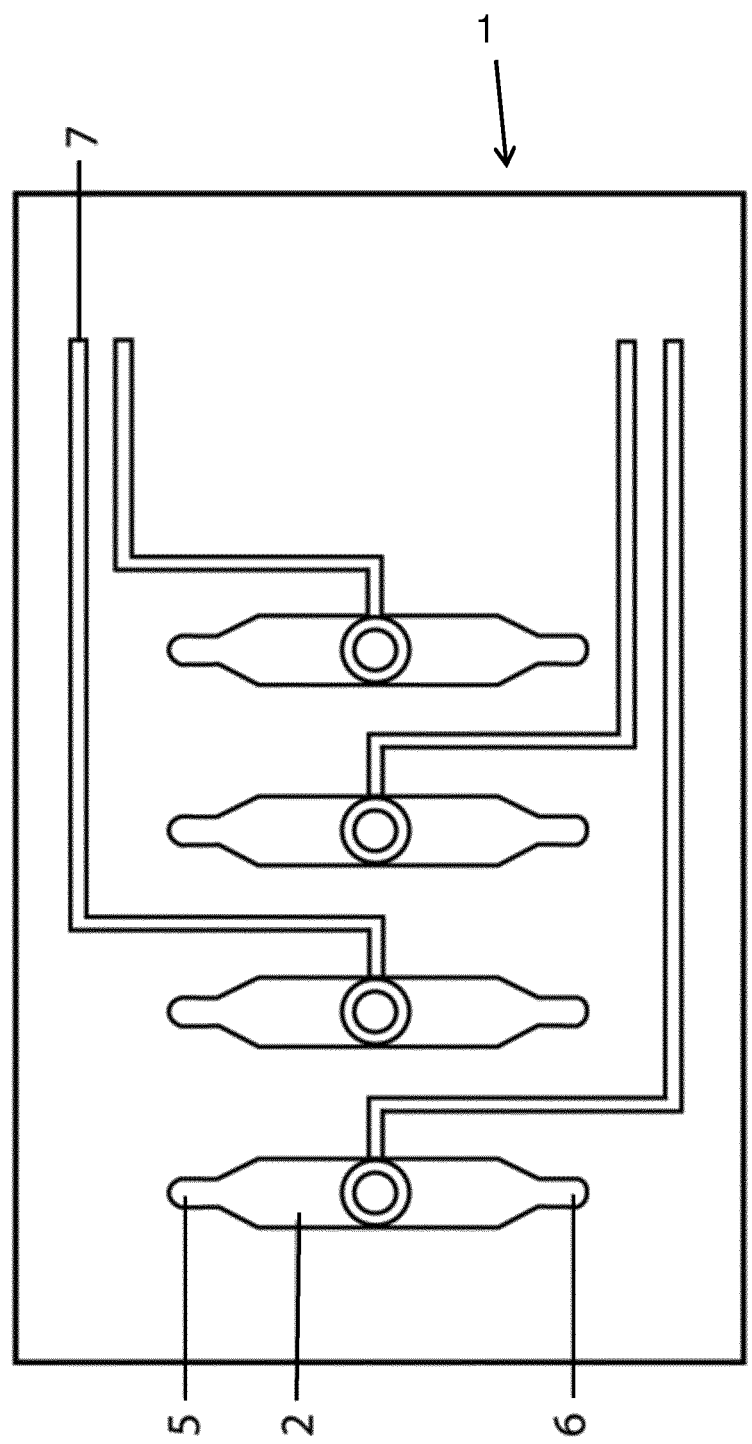
FIG. 4 shows in top view the microfluidic device of FIG. 3.

The microfluidic device 1 has a flat cross section (FIGS. 1 and 3) and elongated shape (FIGS. 2 and 4). The height of the cell chamber 2 is preferably smaller than 1 mm; the width of the cell chamber 2 amounts preferably between 200 µm and 5 mm; and the length of the cell chamber 2 amounts preferably between 2 mm and 10 cm.

The microfluidic devices 1 according to the embodiments shown each comprise four cell chambers 2. However, in order to perform more tests at the same time also a corresponding plurality of cell chambers 2 may be formed within the same plate or substrate.

The present invention is further illustrated in the following examples, however, without being restricted thereto.

EXAMPLES

Material and Methods

Cell Culture Handling and Protein Coating

Lentivirally transduced GFP HUVEC (human umbilical vain endothelial cells) were obtained from Olaf pharmaceuticals (USA) and cultivated in gelatin coated 25 cm$^2$ cell culture flasks and maintained in EGM-2 (Lonza, CC3156) supplemented with EGM-2 SingleQuots (Lonza, CC4176).

The coating was performed using 1% gelatin solution (9000-70-8, Sigma Aldrich) in DPBS and was incubated for 30 min at 37° C. For on chip experiments the medium was supplemented with 1% hepes buffer (J848, AMRESCO). For the coating experiment 500 mM NaOH was inserted to the microfluidic channels, incubated for 15 min at RT, following rinsing with PBS and a protein mixture comprising 10 μg/m fibronectin (Sigma Aldrich, F4759) and 5 μg/μl fibrinogen conjugated with Alexa Fluor 488 (Thermo Fisher, F13191) was incubated for 1 h at 37° C.

For the scratch comparison in the 24-well plate identical coating mixtures was directly applied and incubated for 1 h at 37° C. Dead staining was performed using 2 μM ethidium homodimer-1 (Life Technologies, L3224) supplemented to the cell medium and incubated for 30 min.

Experimental Setup

The microfluidic device of example 1 was placed on a heating plate equipped with a temperature controller. The temperature of the plate was adjusted to reach 37° C. on top of the microdevice. For the on-chip wound healing assays the microchip was first sterilized using 70% ethanol, rinsed using a 1 M NaOH solution for 15 min and washed with PBS prior coating using a 1% gelatin solution for 1 h. Cell suspension of desired concentration was prepared and inserted into microchannels using plastic syringe (1 ml). Cells were allowed to adhere for 1 h in the absence of fluid flow followed by a constant medium perfusion of 4 μl/min using syringe pump. As soon as the cells were grown confluent (typically 1 to 2 days) cells were mechanically damaged ("squeezed") by the PDMS membrane, which bended under force towards the cell layer. Bending was induced by manual increase of pressure load to 150 kPa (differential pressure) followed by immediate release to 0 kPa using a pressure controller. To further remove residual cell debris from the substrate multiple membrane deflections (minimum of three times) were performed. During the mechanical damaging the medium perfusion was always kept on.

Fluorescence Microscopy

Fluorescence images were taken using a Wilovert AFL30 fluorescence microscope (Hund Wetzlar, Germany) equipped with a DSQi1Mc digital camera. All conventional fluorescence images were processed using NIS-elements software (Nikon).

Quantification of Cell Migration

The fluorescence pictures were transformed to grey scale, the contrast increased and the leading edge of the wound selected using the Magic wand tool. This image was then processed using ImageJ by determining the cell-free area with the tool Analyze Particles.

Example 1: Fabrication of Cell Depletion and a Cell Exclusion Based Microdevices for Cell Migration and Wound Healing Studies Microdevice architectures were designed for either cell depletion or cell exclusion using on/off operation of the pneumatically-activated flexible membranes. Both devices were maintained under minimum pressure conditions prior and after wounding to eliminate microbubble formation when using the gas permeable PDMS membrane. The application of mechanical damage to a cell layer in the cell depletion microdevice was accomplished by deflection of a polymeric membrane in between of two microchannels (FIG. 1) while a microstencil confined the cell growth in the cell exclusion device (FIG. 3). As shown in FIGS. 1 and 3 both microdevices consisted of three layers; the top pneumatic layer was used for actuation of the flexible PDMS membrane, while the fluidic chamber was defined by either the bottom layer or middle layer for cell depletion and cell exclusion device, respectively. The circular shaped frame in the pneumatic layer was designed to be 1.5 mm and 2.5 mm in diameter for the cell depletion and cell exclusion device, respectively. All fluidic and pneumatic channels were 90 μm high, while the cultivation chamber was 2.5 mm in width. The microdevice consisted of four parallel cell culture chambers each containing a membrane-deflection area located at the centre, while membrane deflection was separately activated by external pressure control.

Figure 5:
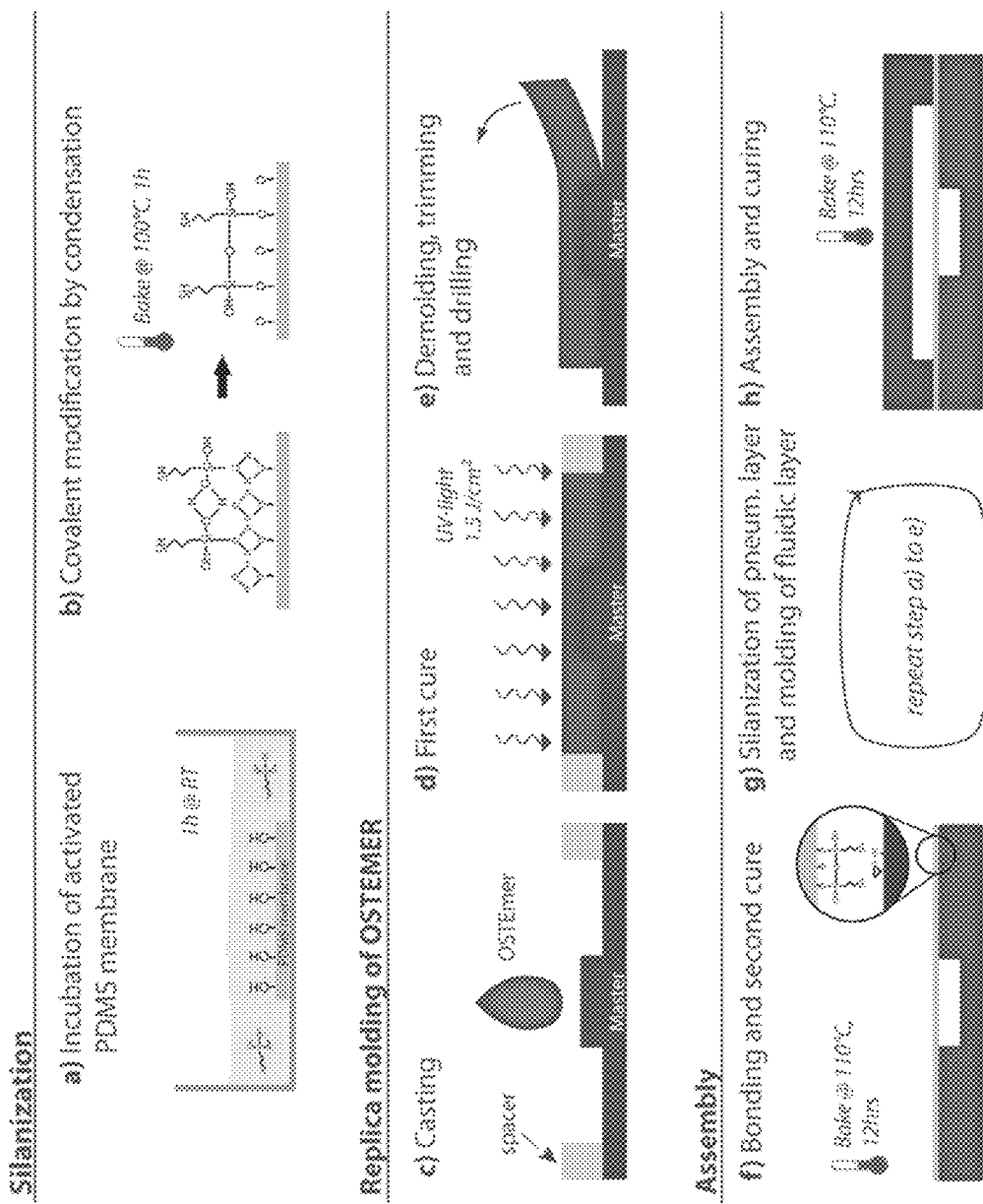
FIG. 5 shows a flow diagram of the microfabrication process steps (see example 1) including silanization (a-b), fabrication of fluidic and pneumatic layer with OSTEMER thermoset (c-e), membrane bonding and device assembly (f-h).

The cell depletion microdevice was fabricated in a multilayered manner consisting of a replica molded dual-cure thermoset defining pneumatic and fluidic microchannels while a PDMS membrane was sandwiched in between both layers. Briefly, the 250 μm thick PDMS membrane (HT-6240, Silex, UK) was corona treated for approximately 30 sec using a Tesla coil (BD-20V, ETP, USA) and incubated for 1 h at room temperature (RT) either in a 5% 3-mercaptopropyltrimethoxysilane (MPTMS) (AB111219, abcr GmbH, Germany) or 5% (3-aminopropyl) triethoxysilane (APTES) (A3648, Sigma Aldrich) solution diluted in absolute ethanol (FIG. 5a). Covalent linkage of the silane to the hydroxyl groups was accomplished by condensation reaction during a period of 1 h at 100° C. (FIG. 5b).

The master moulds for the fluidic and pneumatic layer were fabricated using dryfilm resist (DFR) TMMF 52045 (Tokyo Ohka Kogyo Co., Ltd). Prior lamination silicon wafers were sonicated in 2% Hellmanex III solution (Hellma Analytics), ddH$_2$O and isopropanol for 10 min at 30° C. Two layers of DFR were laminated to the wafer under heat using a HeatSeal H425 A3 office laminator (GBC) to achieve 90 μm high structures. Following lamination, a polymer film mask (Photo Data Ltd, UK) was applied onto the DFR and exposed to 700 mJ/cm$^2$ UV light using a mask aligner (EVG). Crosslinking of the TMMF was performed at 90° C. for 5 min. The resist was then developed in EBR solvent (PGMEA/1-methoxy-2-propyl-acetate; MicroChemicals) under magnetic stirring until non-crosslinked TMMF was completely removed (typically 120 sec.) followed by isopropanol and ddH$_2$O rinsing. Next, the structure was hard-baked at 200° C. for 1 h. To avoid sticking to OSTEMER, the DFR/silicon wafers were spin-coated with 0.5% Teflon AF (60151-100-6, Dupont) diluted in Fluorinert FC-40 (F9755, Sigma Aldrich) at 3000 rpm for 60 s, and baked for 60 s at 125° C. and 2 min at 175° C. prior usage.

The two components of OSTEMER Crystal Clear 322-40 (Mercene Labs AB, Sweden) were weighted according to the ratio specified by the manufacturer, vortexed for 3 min, bubbles removed by degassing for approximately 20 min and poured on the master mold (FIG. 5c). A conventional PET transparency film was used to cover the precursor and define the layer height by using glass spacers (1.1 mm). UV curing was performed with 365 nm Hg-tubes (Bio-link BLX Crosslinker, Vilber Lourmat) at a dose of 1.5 J/cm$^2$ (FIG. 5d), the OSTEMER was gently delaminated from the master mould (FIG. 5e), cleaned with ethanol, dry boosted and trimmed in shape. Access holes were drilled using a bench top drill press followed by extensive cleaning with ethanol.

The silanized PDMS membrane was carefully applied onto the OSTEMER pneumatic layer and backed over night at 110° C. to achieve covalent bonding between thiols and epoxies (FIG. 5f). Next, the PDMS membrane with the OSTEMER layer bonded onto was silanized as shown in FIG. 5a-b. The fluidic layer was casted in the same manner as the pneumatic one (FIG. 5c-e). Finally, the aligned OSTEMER-PDMS-OSTEMER assembly was fixed using an aluminium manifold. To prevent bonding of the membrane to the fluidic layer an alternating pressure of 25 kPa and −40 kPa during the overnight curing process at 110° C. was applied (FIG. 5h).

The cell exclusion microdevice was fabricated in a similar manner using the same casting and bonding techniques as described above for the cell depletion device. The difference was that the middle fluidic layer was made from spin-coated PDMS to define the cell growth chamber, the membrane and the microstencil. Furthermore, as a substrate material glass was used instead of OSTEMER. Briefly, a 1:10 mixture of PDMS (Sylgard 184) was degassed and spin coated at 350 rpm for 60 sec on a DFR-structured (90 µm high) silicon mold to achieve a 300 µm thin structured polymer layer after polymerization at 65° C. for 3 h. Following, the PDMS layer was corona treated and the OSTEMER pneumatic layer was bonded above. For sealing the microchannel, the PDMS layer and a glass substrate were corona treated, aligned and backed at 65° C. over night.

An overview of the two microfluidic devices manufactured as described above and used for studying migration and wound healing is shown in FIGS. 1 to 4. The microfluidic and pneumatic layouts shown in these figures are designed to form a microfluidic cultivation chamber containing an embedded circular shaped, bendable membranes or microstencils located in the centre of the microfluidic top layer. The microdevices were fabricated using a simple two step replica moulding technique shown in FIG. 5. The microdevice designed for cell depletion assays is shown in FIGS. 1 and 2 and was fabricated by covalently bonding a 250 µm thick PDMS membrane in between of two layers of a thiol-ally, epoxy thermoset sheets. The final microdevice sizes were 3 cm×5 cm and consisted of four cultivation chambers, each containing an individually addressable deflection membrane used for mechanical (compressive) cell removal. FIGS. 3 and 4 show the final cell exclusion microdevice containing a removable stamp in the centre of the microfluidic cell culture chamber. Proof-of-principle of device operation is demonstrated using water-soluble dyes, where inflow of the ink is prevented by the presence of the flexible stamp. In turn the application of negative pressures above −20 kPa to the pneumatic lines lifted the stamp resulting in a uniform distribution of the dye.

Example 2: Characterization of Planar Pneumatically-Actuated Membrane Deflection Method for Mechanically Removal of Adherent Cells Initial microdevice evaluation included the ability of the microdevice to repeatedly withstand high internal pressures. To determine the robustness of the membrane-integrated microdevice the bonding strength between PDMS membrane and OSTEMER microfluidics was investigated. In an initial comparative analysis bonding strength of differently treated PDMS membranes to OSTEMER plastic sheets were investigated using an Φ1 mm drilled hole that was covered with covalently bonded membranes. The applied PDMS surface measures included corona treatment and silanization procedures using thiol- and amino-end groups. Silanization of PDMS following corona treatment using amio- (APTES) and thiol- (MPTS) end groups significantly increased the delamination pressure above 200 kPa. This means that apparent bonding strength between modified PDMS membrane and OSTEMER substrate is high enough to allow robust and repeated operation of the microdevice using actuation pressures up to 200 kPa.

To further evaluate membrane deflection behaviour within the assembled microdevice the fluidic microchannel was filled with fluorescein and fluorescence intensity was measured across the deflection zone during pneumatic actuation. Results clearly reveal how the membrane deflects towards the bottom of the microfluidic channel, resulting in the displacement of the water-soluble dye fluorescein and fluorescence intensity decreases over the deflection zone. In the presence of increasing load pressures the fluorescence intensity significantly decreased in the centre of the membrane, thus pointing at a circular deflection zone.

Example 3: Microfluidic Migration Assay Based on Mechanically Creating Cell Depletion Zones of Defined and Highly Reproducible Cell-Free Areas Surface modifications are advantageous when using sensitive cell types such as human umbilical vain endothelial cells (HUVECs) that may require defined protein coatings (e.g. gelatine, fibronectin) that allow for cell migration. Consequently, adequate surface functionality should be provided that fosters cell adhesion and thus promotes cellular movement into the cell-free areas. To assess whether applied protein coatings remain at the surface of the cell-free area after multiple membrane deflections, the microfluidic channel was coated using fluorescent labelled proteins. In a comparative study, fluorescence intensities of Alexa Fluor 488 conjugated fibrinogen coated surfaces were determined prior and after mechanically inducing wounds using both the pneumatically-actuated membrane deflection method and a standard scratch assay. Images taken after mechanically inducing wounds using the scratch assay method demonstrated that almost the entire surface coating was removed from the cell culture substrate, while the microfluidic membrane deflection/compression method showed no visible removal of the applied surface coating. The ability to maintain an intact surface coating during cell removal is advantageous for cell migration, since a variety of anchorage dependent cell types rely on the availability of proper surface coatings to cell migration dynamics.

Next the ability to create defined and reproducible cell depletion zones within a confluent cell monolayer was evaluated using the membrane deflection method. In a series of experiments endothelial cells were seeded and cultivated in a microfluidic channel for a minimum period of 6 hours prior cell removal. During the entire wound healing assay including the cell depletion procedure the applied flow rate of 3 µl/min was kept constant to ensure complete removal of cell debris following membrane compression. In addition to maintaining an intact coating, a further aspect that may also influence cell migration is associated with the release of biochemical factors from viable but injured cells at the edge of the wounding area. To investigate whether cells located in the adjacent vicinity of the cell-free area are injured by membrane compression, dead staining using ethidium homodimer-1 was conducted in subsequent experiments. Results indicated the presence of red fluorescently labelled DNA debris present in the cell-free area following 1 h after wound induction. More importantly, none of the leading edge cells appeared damaged by the membrane compression, since only DNA from lysed cells inside the wound remained on the substrate. These results indicated that cell migration using membrane deflection method is neither influenced by surface coating removal nor by the presence of injured and dead cells at the edge of the wound area.

Since wound healing assay reproducibility strongly depends on the ability to reliably induce wounds of defined cell-free areas, mechanically induced wounds of 18 independent experiments were analysed and compared to standard scratch assay results. Results of this comparative study are shown in FIG. 6 where cell-free area variations were calculated using 'analyse particle' tool from ImageJ. When manually removing cells using a 200 µl pipet tip two spatially separated regions along each scratch was analysed exhibiting large size deviations between cell-free areas within and between individual scratches as shown in FIG. 6B. The obtained average cell-free area of 1.136 mm$^2$ using manually inducing wounds exhibited a standard deviation of 0.229 mm$^2$ or 22% RSD. In turn, automated induction of circular wound areas using the membrane deflection method resulted in an average cell-free area of 0.91 mm$^2$ with a standard deviation of 0.04 mm$^2$ or 4% RSD. This means that in addition to providing spatially defined single circular wounds within a cell monolayer, a 5-fold improvement in assay reproducibility is accomplished when using the pneumatically-actuated membrane deflection method. To further characterize cell migration behaviour of our microfluidic device microscopic images of the mechanically induced wound areas were taken every 12 h and compared to the standard scratch assay. To assess cell migration behaviour into the cell-free areas time-dependent wound area decreases are plotted in FIG. 6C featuring significantly faster healing progression using the membrane deflection method than with the scratch assay. While the membrane compression method resulted in complete wound closure after 24 h, 36 h was needed when employing the scratch assay method. The improved healing kinetic of the membrane deflection method can be associated with the elimination of surface damages and the creation of smaller wound areas.

In a further set of experiments, the microfluidic wound healing assays was used to study the influence of an inflammatory microenvironment on endothelial cell migration. For instance, it is known that cytokines regulate important phases of in vivo wound healing and that elevated TNF-α levels are also present in chronic wounds. To mimic a pathological chronic wound environment the cell culture medium was supplemented with 1 ng/ml TNF-α immediately after mechanical wound induction and maintained over the entire wound closure period. In a comparative study the wound healing progress was followed at 0, 6, 12 and 24 h after cell removal in the absence and presence of TNF-α and Mitomycin-C, respectively. In the case of normal healing already after 6 h of cell migration the wound area decreased by a factor of 10 resulting in a complete closure of the induced wound at 24 h where only a confluent epithelial cell layer was visible. In the presence of the inflammatory factor TNF-α, however, the remaining cell-free area was by a factor of 3.3 larger 6 h-post wounding than observed with control experiments. To further determine whether cell migration and/or cell proliferation was the dominant contributor to wound closures in microfluidic systems the cell proliferation inhibitor Mitomycin-C was added to the cell culture medium. Based on initial proliferation inhibition studies 10 µg/ml Mitomycin-C was used in the experiment to limit wound healing mainly to cell migration. In an experimental setup HUVEC healing dynamics were monitored following an one hour exposure of the proliferation blocker at a flow rate of 3 µl/min. Surprisingly, the obtained cell-free area after 6 h was 5 times larger compared to the control experiments and 1.5 times larger compared to TNF-α treated cells. This result indicates that cellular uptake of 10 µg/ml Mitomycin-C also negatively influences endothelial cell migration, since the doubling time of HUVECs was estimated to take up to 2 days. Although wound closure was observed after 24 h, cell density within the wounded area is visibly reduced compared to control, thus suggesting that cell proliferation might be a contributing factor in the late stages of wound healing.

These results show impressively the advantages of the microfluidic migration and wound healing assay of the present invention containing substantially planar, flexible membranes and removable microstencils to mechanically induce highly reproducible wounds within confluent cell cultures. In the present examples a mechanical cell depletion approach based on membrane deflection/compression was characterized and evaluated against the gold-standard scratch assay. Results obtained demonstrate that the combination of a membrane deflection/compression technology with microfluidic cell cultures overcomes existing problems such as multiple wounding of the same area during perfusion, which efficiently removes cell debris from the cell-free areas. Moreover, the automation, miniaturization and integration of wound healing assays in microfluidic devices promises a wide range of applications including (a) chemotaxis by applying chemical gradients, (b) migration studies using surface sensitive cell types, (c) repeated wounding, and (d) cyclic compressive stress tests on cell monolayers as well as (e) mechanical actuation of 3D-hydrogel based microfluidic cell cultures by simply controlling applied air pressures.

Characterization of the microfluidic membrane deflection method revealed that pneumatic compression of a flexible PDMS membrane creates highly reproducible (RSD of 4%) circular shaped cell-free areas with neglectable amounts of injured cells along the wound edge. Additionally, it was demonstrated that applied biofunctionalization and ECM coatings remain intact on the substrate after mechanical cell removal, thus promoting reliable and unaltered cell migration into the wound. Furthermore, the microfluidic removal of cell debris from the depletion zone ensures highly uniform migration conditions between wound healing assays. All of the above features are advantageous for cell migration that leads to improved assay performance including assay time, reproducibility and robustness. Practical application of the microfluidic wound healing assay was demonstrated for studying normal and pathological wound healing dynamics.

The invention claimed is:

1. A microfluidic device for creating within a cell assembly a cell-free area, comprising at least one cell chamber, wherein the at least one cell chamber comprises:
   a fluid inlet for introducing fluid into the cell chamber,
   a top layer, an intermediate layer formed from a flexible membrane material, and a bottom layer, and
   a first area and a second area disposed on an inner surface of the bottom layer,
   at least one mechanical excluding means formed by the intermediate layer and configured for excluding cells from the first area of the chamber and being operable between an excluding position and a releasing position via an actuation line, the actuation line being formed in the top layer and providing fluid communication with the intermediate layer to enable actuation of the mechanical excluding means via pressure, wherein the second area of the cell chamber is outside of the operation range of the mechanical excluding means, and wherein the first area is substantially completely surrounded by the second area.

2. A microfluidic device according to claim 1, wherein the mechanical excluding means abuts in its excluding position against the bottom layer.

3. A microfluidic device according to claim 1, wherein the inner surface of the bottom layer opposite to the mechanical excluding means is substantially planar.

4. A microfluidic device according to claim 1, wherein the inner surface of the bottom layer opposite to the mechanical excluding means is coated with at least one polypeptide and/or peptide.

5. A microfluidic device according to claim 1, wherein the membrane comprises polydimethylsiloxane (PDMS), thi-ol-ene-epoxy based polymers, fluorinated ethylene-propylene or a combination thereof.

6. A microfluidic device according to claim 1, wherein the actuation line is a pneumatic line or a fluid line.

7. A microfluidic device according to claim 4, wherein the at least one polypeptide and/or peptide has at least one cell adhesion promoter.

8. A microfluidic device according to claim 7, wherein the cell adhesion promotor is selected from the group consisting of fibronectin, fibrinogen, gelatin, collagen, laminin, poly-D-lysine and mixtures thereof.

9. A microfluidic device according to claim 5, wherein the membrane further comprises a ferromagnetic coating and/or ferromagnetic particles.

10. A microfluidic device according to claim 1, wherein the second area is outside of the operation range of any mechanical excluding means of the cell chamber.

11. A kit comprising a microfluidic device according to claim 1 and a microscope and/or a pump system.

12. A method of using a microfluidic device according to claim 1, comprising monitoring cell migration or performing a cell migration assay.

13. A method for monitoring cell migration of human or animal cells, in particular of mammalian cells, comprising the steps of:
   a. applying cells into the least one cell chamber of the microfluidic device according to claim 1 to cover the second area,
   b. bringing the mechanical excluding means in an excluding position via the actuation line to displace or remove the cells from the first area,
   c. bringing the mechanical excluding means in a releasing position via the actuation line, and
   d. allowing cell migration and monitoring cell migration.

14. A method according to claim 13, wherein cell migration is monitored by microscopy.

15. A method according to claim 13, wherein the cells are stained with a stain selected from the group consisting of Hoechst, Hoechst 33258, Hoechst 33342, Hoechst 34580, Calcein, Calcein AM, Calcein Blue, Calcein Blue AM, Calcium Green 1, Calcium Green 2, Calcium Gwnreen 5N, CoroNa Green, CoroNa Green AM, CoroNa Red, DiL, Fluo 3, Fluo 3 AM, Fluo 4, Fluo 4 AM, fluorescein dextran, Carboxyfluorescein succinimidyl ester (CFSE), and Texas Red dextran.

16. A method according to claim 13, wherein the cells are genetically modified to express marker proteins.

17. A method according to claim 13, wherein the cells are selected from the group consisting of endothelial cells, epithelial cells, fibroblasts, neurons, glial cells, stem cells, fat cells muscle cells and cancer cells.

18. A method according to claim 13, wherein in step a the cells are applied into the at least one cell chamber of the microfluidic device to cover the second area and the first area.

19. A method according to claim 14, wherein cell migration is monitored by fluorescence microscopy or phase-contrast microscopy.

20. A method according to claim 16, wherein said marker proteins are fluorescent marker proteins.

21. A method according to claim 17, wherein the cells are adherent cells.

* * * * *